United States Patent [19]

Biere et al.

[11] Patent Number: 4,503,049

[45] Date of Patent: Mar. 5, 1985

[54] DIPHOSPHONIC ACID DERIVATIVES AND PHARMACEUTICAL PREPARATIONS CONTAINING THEM

[75] Inventors: Helmut Biere; Clemens Rufer, both of Berlin, Fed. Rep. of Germany; Irmgard Boettcher, Basel, Switzerland

[73] Assignee: Schering Aktiengesellschaft, Berlin and Bergkamen, Fed. Rep. of Germany

[21] Appl. No.: 461,411

[22] Filed: Jan. 27, 1983

[30] Foreign Application Priority Data

Jan. 27, 1982 [DE] Fed. Rep. of Germany ....... 3203308

[51] Int. Cl.³ .................. A61K 31/66; A61K 33/665; C07F 9/38; C07F 9/65
[52] U.S. Cl. ..................................... 514/80; 260/932; 548/113; 548/119; 548/414; 549/220; 514/90; 514/91; 514/92; 514/94; 514/100; 514/102; 514/107; 514/108
[58] Field of Search ................ 260/932; 548/113, 119, 548/414; 549/220; 424/200, 203, 204

[56] References Cited

FOREIGN PATENT DOCUMENTS 2079285 1/1982 United Kingdom .

OTHER PUBLICATIONS

Worms et al., J. Anorg. Allg. Chem., vol. 457, (1979), pp. 209–213.

Primary Examiner—Richard L. Raymond
Attorney, Agent, or Firm—Millen & White

[57] ABSTRACT

Diphosphonic acid derivatives of Formula I

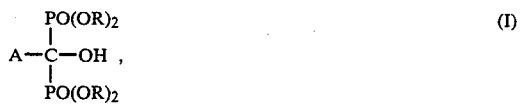

wherein

R is hydrogen, an alkali metal atom, an alkaline earth metal atom, or an alkyl group of 1–4 carbon atoms and A is derived from a carboxylic acid having anti-inflammatory and antiphlogistic activity and containing an aromatic or heteroaromatic group, of Formula II

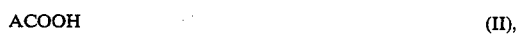

are pharmacologically efficacious compounds.

18 Claims, No Drawings

DIPHOSPHONIC ACID DERIVATIVES AND PHARMACEUTICAL PREPARATIONS CONTAINING THEM

The present invention relates to diphosphonic acid derivatives and to pharmaceutical preparations containing them as active ingredients.

SUMMARY OF THE INVENTION

It is an object of the invention to provide new compounds having valuable pharmacological properties.

Upon further study of the specification and appended claims, further objects and advantages of this invention will become apparent to those skilled in the art.

These objects have been attained by providing diphosphonic acid derivatives of Formula I

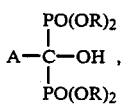          (I)

wherein

R is hydrogen, an alkali metal atom, an alkaline earth metal atom, or alkyl of 1–4 carbon atoms and A is the residue of a carboxylic acid having anti-inflammatory and antiphlogistic activity, containing an aromatic or heteroaromatic group and being of Formula II

ACOOH          (II);

diphosphonic acid derivatives of Formula Ia

          (Ia)

wherein

R is as defined for Formula I,

X is hydrogen, methyl, or ethyl, and

B is phenyl substituted in the para-position by isobutyl, cyclohexyl, alkoxy, or 1-pyrrolinyl and, optionally, substituted additionally in the meta-position by fluorine or chlorine; or phenyl substituted in the meta-position by benzoyl or phenoxy, or phenyl substituted in the ortho-position by 2,4-dichlorophenoxy or 2,6-dichlorophenylamino;

diphosphonic acid derivatives of Formula Ib

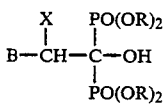          (Ib)

wherein

R is as defined in Formula I, $R^1$ is cyclohexyl or cyclopentylmethyl; and

Y is hydrogen or chlorine;

diphosphonic acid derivatives of Formula Ic

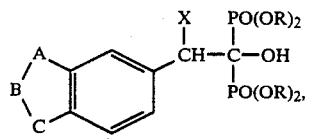          (Ic)

wherein

R and X are as defined above, and

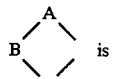 is

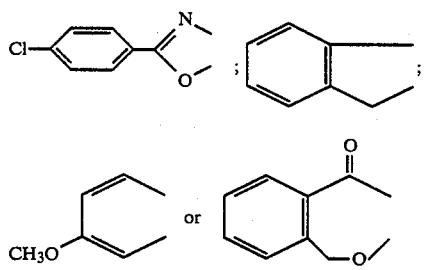

diphosphonic acid derivatives of Formula Id

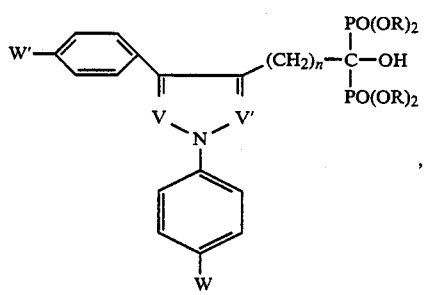          (Id)

wherein n is 1, 2, or 3,

R is as defined in Formula I,

W and W', are identical or different, and each is hydrogen, fluorine or chlorine, and one of V and V' is nitrogen and the other is a methyne residue optionally substituted by a phenyl group; and diphosphonic acid derivatives of Formula Ie

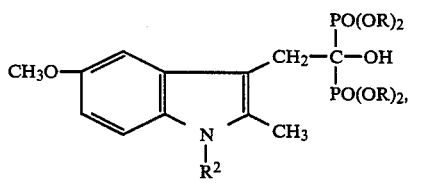          (Ie)

wherein

R is as defined in Formula I, and $R^2$ is p-chlorobenzoyl or cinnamoyl;

or, throughout, when R is H, a physiologically acceptable salt thereof with an organic base.

DETAILED DISCUSSION

In the foregoing formulae, suitable cations include Na, K, Ca, Ba, Sr, Mg, etc. and suitable alkyl groups include methyl, ethyl, the propyls and the butyls. In B, the alkoxy groups generally have 1-4 C-atoms.

The phosphonic acid derivatives of Formula Ia are derived from carboxylic acids having antiinflammatory and antiphlogistic activity, of Formula II, which are known by their antiinflammatory effectiveness, such as, for example, ibuprofen, butibufen, MK 830, fluorbiprofen, alclofenac, pirprofen, ketoprofen, fenoprofen, fenclofenac, or diclofenac. Carboxylic acids of a similar structure and of good antiinflammatory activity, which are likewise suitable for the preparation of diphosphonic acid derivatives of Formula I include for example, cliprofen, suprofen, or indoprofen.

The compounds of Formula Ib are likewise derived from carboxylic acids also distinguished by a good antiinflammatory and antiphlogistic activity, for example, BL 2365, clidanac, or 6-chloro-5-cyclopentylmethyl-1-indanecarboxylic acid.

The carboxylic acids forming the basis for the phosphonic acid derivatives of Formula Ic are, as is known, likewise of similarly good effectiveness, for example, benoxaprofen, cicloprofen, naproxen, or isoxepac. Similarly highly effective carboxylic acids, which are likewise suitable for preparing diphosphonic acid derivatives of Formula I, are carprofen and metiazic acid.

Suitable starting materials for the production of the diphosphonic acid derivatives of Formula Id include, for example, trifezolac, pirazolac, or lonazolac. Structurally similar phosphonic acid derivatives of Formula I can be prepared by reacting antiinflammatorily and antiphlogistically active carboxylic acids of Formula II, for example, bufezolac or isofezolac.

The phosphonic acid derivatives of Formula Ie are derived, for example, from the highly effective carboxylic acids such as indomethacin or cinmetacin.

Other highly active carboxylic acids of Formula II likewise suitable for producing phosphonic acid derivatives of Formula I include, for example, tiaprofenic acid, zomepirac, tolmetin, clopirac, fenclozic acid, fentiazac, or sulindac, etc.

Especially preferred compounds are those of the Formulae Ia-Ie and the examples below.

As can be seen, there are many compounds of Formula II which are antiinflammatorily or antiphlogistically active which can provide A groups which are contemplated equivalents of the specific such groups exemplified herein. All of these are included in this invention. In essence, this invention provides a structural modification to acids ACOOH by which they are made to possess the advantageous properties described herein. Many such acids of the Formula A—COOH and possessing the requisite antiinflammatory or antiphlogistic activity are known and described in T. J. Shen, Nonsteroidal Anti-inflammatory Agents in Burger's Medicinal Chemistry 4. Ed. 1981, Part III, pages 1205-1272.

The compounds of this invention, as do the carboxylic acids of Formula II $$A—COOH \quad (II),$$

exhibit pronounced antiinflammatory and antiarthritic activity. However, the compounds of this invention are distinguished over these compounds in that they are capable, inter alia, to affect the productive and destructive power of bone cells (osteoblasts/osteoclasts) in such a way that curative effects can clearly be proven to exist in rats with induced arthritis.

This antiarthritic activity of the compounds of this invention forms the basis for therapy of rheumatoid arthritis, osteoarthritis, ankylosing spondylitis, and other related diseases, especially of the collagen and the skeletal system (e.g., osteoporosis, Paget's disease, etc.). Moreover, the phosphonates can be utilized in a therapeutically meaningful fashion as good complexing agents for calcium in all cases where a disturbed calcium metabolism has been recognized as cause for a disease, for example in cardiovascular disorders, ectopic calcifications, etc.

The compounds can be employed in the form of their full alkyl esters, di-monoesters (half esters)—but preferably in the form of the free phosphonic acids and/or their physiologically compatible salts with alkali or alkaline earth hydroxides or with compatible organic bases, eg. sodium hydroxide, potassium hydroxide, calcium hydroxide, piperazine or methylglucamine.

Suitable galenic formulations for enteral or parenteral administration include capsules, tablets, dragees, suppositories, and also injection solutions and dermal preparations. Also, local application is possible for the treatment of dermal or systemic diseases.

The medical specialties are prepared in the usual way by converting the active agents into the desired forms of application with suitable additives, e.g., solutions, lotions, ointments, creams, or plasters. In the thus-formulated medicines, the concentration of active compound is dependent on the type of application. In the case of lotions and ointments, an active agent concentration of 0.1% to 10% is preferably employed. Administration is as conventional with such topical formulations, e.g., as with a hydrocortisone cream.

The novel corticoids are also suitable furthermore in the form of capsules, tablets, or dragees, etc., containing preferably 10-500 mg of active agent and being administrable orally (e.g., at daily dosages of 1-50 mg/kg), e.g., analogously to the known agent indometacine or naproxene.

Conventional excipients are pharmaceutically acceptable organic or inorganic carrier substances suitable for parenteral, enteral or topical application to mammals, including humans, which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Dosages for a given host for a given indication can be determined, e.g., by customary comparison of the activities of the subject compound and of a known agent by means of an appropriate, conventional pharmacological protocol.

The phosphonates of this invention can be prepared according to methods which are well known to those skilled in the art and disclosed, e.g., in Houben-Weyl, "Methoden der organischen Chemie" (Methods of Organic Chemistry) Georg Thieme publishers, Stuttgart, 4th edition (1963) XII/1: 453 et seq. whose disclosures are incorporated by reference herein; such methods are represented in the schematic below wherein an acyl phosphonate of Formula III $$A-COPO(OR)_2 \qquad (III)$$

wherein A, and R are as defined above, is reacted in the presence of a base, with a dialkyl phosphite of Formula IV $$HPO(OR)_2 \qquad (IV)$$

wherein R is as defined above, and optionally saponifying the thus-formed esters, and optionally converting the acids into the salts thereof.

SCHEME (a) ACOCl  A—COPO$_3$R$_2$

HPO$_3$R$_2$
Base

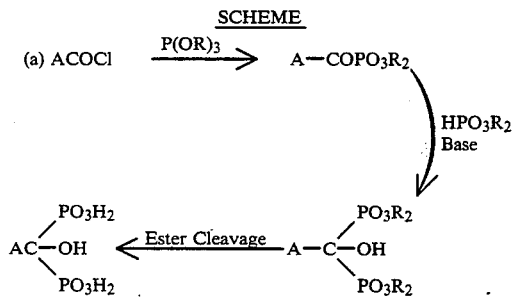

Examples of bases suitable for conducting the process of this invention include secondary amines, e.g., diethylamine, dipropylamine, diisopropylamine, morpholine, or piperidine. The reaction is conducted in inert organic solvents, e.g., ethers (e.g. diethyl ether, diisopropyl ether, dioxane, tetrahydrofuran) or chlorinated hydrocarbons (e.g. dichloromethane, tetrachloroethane, chloroform, or carbon tetrachloride).

The optionally subsequently effected saponification of the esters can take place with mineral acids (e.g. semiconcentrated hydrochloric acid or sulfuric acid). The cleavage reaction occurs in an especially gentle fashion in an inert solvent (for example one of the above-mentioned chlorinated hydrocarbons) with trimethylsilyl iodide. For the salt formation, the free acids are reacted as usual conventionally with the corresponding bases.

The starting compounds of Formula II required for the process of this invention can be prepared conventionally from the corresponding acid chlorides by reaction with dialkyl phosphites of Formula III. The acid chlorides are all known or fully conventionally preparable.

These syntheses illustrated in the schematic chart will be explained in greater detail in the following practical examples with reference to typical representatives.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

EXAMPLE 1

At $-7°$ C., a suspension of 3.70 g of 2-[1-(4-chlorobenzoyl)-5-methoxy-2-methyl-3-indolyl]-1-hydroxyethene-phosphonic acid dimethyl ester (U.S. Pat. No. 4,014,997) in 20 ml of tetrahydrofuran is combined with a solution of 1.08 g of dimethyl phosphite and 0.63 g of diethylamine and allowed to stand for 3 hours at $-7°$ C. and then 16 hours at $-15°$ C. The thus-precipitated product is then vacuum-filtered, thus obtaining 3.2 g of 2-[1-(4-chlorobenzoyl)-5-methoxy-2-methyl-3-indolyl]-1-hydroxyethane-1,1-bis(phosphonic acid dimethyl ester), mp 163° C.

EXAMPLE 2

16.6 g of 2-(6-methoxy-2-naphthyl)propionic acid is stirred in 200 ml of diethyl ether with 16.2 g of phosphorus pentachloride for 60 minutes at 20° C. The mixture is then concentrated, the residue triturated with petroleum ether, and the product is 18 g of 2-(6-methoxy-2-naphthyl)propionyl chloride, mp 95° C.

6.66 g of this acid chloride is combined in 100 ml of diethyl ether with 3.99 g of trimethyl phosphite at 20° C. and stored for 16 hours. The mixture is then concentrated and the residue crystallized from diisopropyl ether, thus obtaining 3.63 g of 2-(6-methoxy-2-naphthyl)propionylphosphonic acid dimethyl ester, mp 59° C.

A suspension of 5.0 g of this phosphonic acid ester in 70 ml of diethyl ether is combined with 1.42 g of dimethyl phosphite and, at $-10°$ C., with 0.26 g of dibutylamine in 10 ml of diethyl ether. The mixture is cooled for 2 hours at $-5°$ C., the crystallized product is vacuum-filtered, and the thus-obtained product is 4.46 g of 2-(6-methoxy-2-naphthyl)-1-hydroxypropane-1,1-bis(-phosphonic acid dimethyl ester), mp 140° C.

EXAMPLE 3

4.66 g of 2-(4-isobutylphenyl)propionic acid is agitated in 150 ml of diethyl ether with 5.04 g of phosphorus pentachloride for one hour at 20° C. The mixture is then concentrated under vacuum, thus obtaining 5.02 g of 2-(4-isobutylphenyl)propionyl chloride. This compound is reacted with trimethyl phosphite as described in Example 2, thus producing the dimethyl ester of 2-(4-isobutylphenyl)propionylphosphonic acid. The dimethyl ester is reacted with dimethyl phosphite under the conditions described in Example 2, thus obtaining the 2-(4-isobutylphenyl)-1-hydroxypropane-1,1-bis(-phosphonic acid dimethyl ester).

EXAMPLE 4

2.68 g of (11-oxo-2-dibenz[b,f]oxepinyl)acetic acid is dissolved in 9.15 ml of thionyl chloride and heated for 3 hours under reflux. The mixture is then concentrated under vacuum, thus obtaining 3.04 g of (11-oxo-2-dibenz[b,f]oxepinyl)acetyl chloride. This acid chloride is reacted under the conditions of Example 2 with trimethyl phosphite, yielding 1.34 g of 2-(11-oxo-2-dibenz[b,f]oxepinyl)-1-hydroxyethenephosphonic acid dimethyl ester, mp 118° C. The resultant product is reacted with dimethyl phosphite as described in Example 1, yielding the 2-(11-oxo-2-dibenz[b,f]oxepinyl)-1-hydroxyethane-1,1-bis(phosphonic acid dimethyl ester), mp 133° C.

EXAMPLE 5

3.22 g of 6-chloro-5-cyclopentylmethyl-1-indanecarboxylic acid is heated under reflux for one hour with 10.5 ml of thionyl chloride and concentrated, thus yielding 3.45 g of 6-chloro-5-cyclopentylmethyl-1-indanecarboxylic acid chloride as an oil. The acid chloride is reacted with triethyl phosphite as described in Example 2, yielding 3 g of (6-chloro-5-cyclopentylmethyl-1-indanylidene)hydroxymethanephosphonic acid diethyl ester, mp 126° C. The resultant compound is reacted with diethyl phosphite under the conditions mentioned in Example 2, thus obtaining the (6-chloro-5-cyclopentylmethyl-1-indanyl)hydroxymethane-bis(phosphonic acid diethyl ester).

EXAMPLE 6

2-[N-Acetyl-N-(2,6-dichlorophenyl)amino]phenylacetic acid is reacted with phosphorus pentachloride in diethyl ether to obtain 2-[N-acetyl-N-(2,6-dichlorophenyl)amino]phenylacetic acid chloride. The acid chloride is then reacted with trimethyl phosphite under the conditions described in Example 2, thus producing 2-[N-acetyl-N-(2,6-dichlorophenyl)amino]phenyl-1-hydroxyethene-1-phosphonic acid dimethyl ester; this compound is converted, under the conditions of Example 1, with dimethyl phosphite into 2-[2-(2,6-dichlorophenylamino)phenyl]-1-hydroxyethane-1,1-bis(phosphonic acid dimethyl ester).

EXAMPLE 7

2-[2-(2,6-Dichlorophenylamino)phenyl]-1-hydroxyethane-1,1-bis(phosphonic acid dimethyl ester) is heated for 4 hours on a steam bath with concentrated hydrochloric acid; the mixture is then diluted with water, allowed to cool down, and the thus-separated product is vacuum-filtered, thus obtaining 2-[2-(2,6-dichlorophenylamino)phenyl]-1-hydroxyethane-1,1-diphosphonic acid.

EXAMPLE 8

2.18 g of 2-[1-(4-chlorobenzoyl)-5-methoxy-2-methyl-3-indolyl]-1-hydroxyethane-1,1-bis(phosphonic acid dimethyl ester) is combined in 15 ml of tetrachloromethane at −5° C. with 2.29 ml of iodotrimethylsilane and stored for 4 hours at 0° C. The mixture is then concentrated under vacuum and combined with ice water. The thus-obtained precipitate is triturated with acetonitrile and vacuum-filtered, thus obtaining 1.92 g of 2-[1-(4-chlorobenzoyl)-5-methoxy-2-methyl-3-indolyl]-1-hydroxyethane-1,1-diphosphonic acid, mp 202° C.

EXAMPLE 9

Under the conditions of Example 7, 2-(6-methoxy-2-naphthyl)-1-hydroxypropane-1,1-bis(phosphonic acid dimethyl ester) is hydrolyzed, yielding 2-(6-methoxy-2-naphthyl)-1-hydroxypropane-1,1-diphosphonic acid, mp 205° C.

EXAMPLE 10

Under the conditions of Example 7, 2-(4-isobutylphenyl)-1-hydroxypropane-1,1-bis(phosphonic acid dimethyl ester) is hydrolyzed, thus producing 2-(4-isobutylphenyl)-1-hydroxypropane-1,1-diphosphonic acid.

EXAMPLE 11

Under the conditions of Example 7, 2-(11-oxo-2-dibenz[b,f]oxepinyl)-1-hydroxyethane-1,1-bis(phosphonic acid dimethyl ester) is reacted, yielding 2-(11-oxo-2-dibenz[b,f]oxepinyl)-1-hydroxyethane-1,1-diphosphonic acid, mp 228° C.

EXAMPLE 12

(6-Chloro-5-cyclopentylmethyl-1-indanyl)hydroxymethanebis(phosphonic acid diethyl ester) is reacted under the conditions of Example 7, yielding (6-chloro-5-cyclopentylmethyl-1-indanyl)hydroxymethanediphosphonic acid.

EXAMPLE 13

16.5 g of 4-(4-chlorophenyl)-1-(4-fluorophenyl)-3-pyrazoleacetic acid is cooled in 400 ml of diethyl ether to −15° C. and combined with incremental portions of 14.6 g of phosphorus pentachloride. The mixture is stirred at −15° C. for 2.5 hours and at 0° C. for another 2.5 hours. The clear solution is then exhaustively concentrated under vacuum, the oily residue is stirred together with petroleum ether (boiling range 40°–60° C.), and the product is 16 g of 4-(4-chlorophenyl)-1-(4-fluorophenyl)-3-pyrazoleacetic acid chloride, mp 93°–95° C.

A solution of 17.5 g of 4-(4-chlorophenyl)-1-(4-fluorophenyl)-3-pyrazoleacetic acid chloride in 100 ml of tetrahydrofuran is cooled to 10° C. and combined with 9.8 ml of triethyl phosphite. The mixture is stirred for 3 hours at 10°–15° C., the solution is concentrated under vacuum, and the oily residue is crystallized from diisopropyl ether, thus obtaining 18.8 g (83.4%) of 2-[4-(4-chlorophenyl)-1-(4-fluorophenyl)-3-pyrazolyl]-1-hydroxyethenephosphonic acid diethyl ester, mp 96°–98° C.

EXAMPLE 14

At 0° C., a solution of 18 g of 2-[4-(4-chlorophenyl)-1-(4-fluorophenyl)-3-pyrazolyl]-1-hydroxyethenephosphonic acid diethyl ester in 40 ml of tetrahydrofuran is added dropwise to a solution of 5.7 g of diethyl phosphite and 4.6 ml of diethylamine in 30 ml of tetrahydrofuran, and the mixture is stirred for 5 hours at 0°–5° C. The mixture is concentrated under vacuum, recrystallized from diethyl ether and then recrystallized from carbon tetrachloride, thus obtaining 15.2 g (64.4%) of 2-[4-(4-chlorophenyl)-1-(4-fluorophenyl)-3-pyrazolyl]-1-hydroxyethane-1,1-bis(phosphonic acid diethyl ester), mp 141°–142° C.

EXAMPLE 15

11.8 g of 2-[4-(4-chlorophenyl)-1-(4-fluorophenyl)-3-pyrazolyl]-1-hydroxyethane-1,1-bis(phosphonic acid diethyl ester) is stirred for one hour at room temperature with 5 equivalents of iodotrimethylsilane in 50 ml of carbon tetrachloride under nitrogen. The mixture is concentrated under vacuum, the residue is combined with water and acetone, stirred for another 30 minutes, and the thus-precipitated product is recrystallized from ethanol. Yield: 8.0 g (84%) of 2-[4-(4-chlorophenyl)-1-(4-fluorophenyl)-3-pyrazolyl]-1-hydroxyethane-1,1-diphosphonic acid, mp 202°-204° C.

EXAMPLE 16

0.59 g of 2-[4-(4-chlorophenyl)-1-(4-fluorophenyl)-3-pyrazolyl]-1-hydroxyethane-1,1-bis(phosphonic acid diethyl ester) is combined with 4 ml of 63% strength hydrobromic acid and heated for 2 hours to 100° C. The mixture is then diluted with water and allowed to cool down. The resultant crude product is comminuted and recrystallized from ethanol, yielding 0.37 g (77%) of 2-[4-(4-chlorophenyl)-1-(4-fluorophenyl)-3-pyrazolyl]-1-hydroxyethane-1,1-diphosphonic acid, mp 201°-203° C.

EXAMPLE 17

A solution of 1.9 g of 2-[4-(4-chlorophenyl)-1-(4-fluorophenyl)-3-pyrazolyl]-1-hydroxyethane-1,1-diphosphonic acid in 5 ml of dimethylformamide is combined with a solution of 0.8 g of sodium bicarbonate in 10 ml of water and stirred for 2 hours at room temperature. Then the thus-precipitated product is vacuum-filtered, washed with a small amount of water, and dried at 110° C., yielding 1.6 g (76%) of 2-[4-(4-chlorophenyl)-1-(4-fluorophenyl)-3-pyrazolyl]-1-hydroxyethanediphosphonic acid disodium salt, mp above 300° C.

EXAMPLE 18

[3-(4-Chlorophenyl)-1-phenyl-4-pyrazolyl]acetyl chloride is reacted with trimethyl phosphite as described in Example 13 and worked up, thus obtaining, in an 80% yield, the dimethyl ester of 2-[3-(4-chlorophenyl)-1-phenyl-3-pyrazolyl]-1-hydroxyethanephosphonic acid, mp 174° C. (diethyl ether).

EXAMPLE 19

2-[3-(4-Chlorophenyl)-1-phenyl-4-pyrazolyl]-1-hydroxyethanephosphonic acid dimethyl ester is reacted with dimethyl phosphite as described in Example 14 and worked up, thus obtaining in a 69% yield 2-[3-(4-chlorophenyl)-1-phenyl-3-pyrazolyl]-1-hydroxyethane-1,1-bis(phosphonic acid dimethyl ester), mp 130° C.

EXAMPLE 20

2-[3-(4-Chlorophenyl)-1-phenyl-4-pyrazolyl]-1-hydroxyethane-1,1-bis(phosphonic acid dimethyl ester) is reacted as described in Example 15, thus obtaining in a 78% yield 2-[3-(4-chlorophenyl)-1-phenyl-3-pyrazolyl]-1-hydroxyethane-1,1-diphosphonic acid, mp 199° C.

EXAMPLE 21

(a) At 20° C., 2.8 g of malonic acid dimethyl ester is added to a suspension of 0.7 g of 80% sodium hydride in 40 ml of 1,2-dimethoxyethane and the mixture is agitated for 30 minutes. Then a solution of 7.3 g of 3-bromomethyl-4-(4-chlorophenyl)-1-(4-fluorophenyl)-pyrazole in 30 ml of 1,2-dimethoxyethane is added thereto, and the mixture is stirred for another 12 hours. The reaction mixture is worked up as usual, the residue is recrystallized from cyclohexane, and the product is 4.2 g of [4-(4-chlorophenyl)-1-(4-fluorophenyl)-3-pyrazolylmethyl]malonic acid dimethyl ester, mp 123° C.

(b) A solution of 0.9 g of [4-(4-chlorophenyl)-1-(4-fluorophenyl)-3-pyrazolylmethyl]malonic acid dimethyl ester in 2.5 ml of ethanol is combined with 12 ml of 2N aqueous sodium hydroxide solution and heated for 3 hours under reflux. The mixture is allowed to cool, acidified with 2N hydrochloric acid, the precipitate is recrystallized from acetonitrile, and the thus-obtained product is 0.8 g of [4-(4-chlorophenyl)-1-(4-fluorophenyl)-3-pyrazolylmethyl]malonic acid, mp 188° C.

(c) A solution of 3 g of [4-(4-chlorophenyl)-1-(4-fluorophenyl)-3-pyrazolylmethyl]malonic acid in 50 ml of chlorobenzene is heated under reflux until the release of gas ceases (about 2.5 hours). The mixture is concentrated under vacuum, the residue is recrystallized from carbon tetrachloride, thus obtaining 2.2 g of 3-[4-(4-chlorophenyl)-1-(4-fluorophenyl)-3-pyrazolyl]propionic acid, mp 131° C.

(d) At 0° C., 1.3 g of phosphorus pentachloride is added in incremental portions to a mixture of 1.9 g of 3-[4-(4-chlorophenyl)-1-(4-fluorophenyl)-3-pyrazolyl]propionic acid in 60 ml of diethyl ether; the mixture is agitated for 3 hours, then concentrated, and the residue recrystallized from petroleum ether, thus obtaining 1.85 g of 3-[4-(4-chlorophenyl)-1-(4-fluorophenyl)-3-pyrazolyl]propionic acid chloride, mp 111° C.

(e) At 0° C., a solution of 0.7 g of trimethyl phosphite in 2 ml of diethyl ether is added dropwise to a solution of 1.85 g of 3-[4-(4-chlorophenyl)-1-(4-fluorophenyl)-3-pyrazolyl]propionic acid chloride in 10 ml of diethyl ether. The mixture is allowed to stand for 3 days, concentrated under vacuum, and the yield is 1.98 g of 3-[4-(4-chlorophenyl)-1-(4-fluorophenyl)-3-pyrazolyl]-1-oxopropane-1-phosphonic acid dimethyl ester as an oil.

(f) At 0° C., a solution of 1.98 g of 3-[4-(4-chlorophenyl)-1-(4-fluorophenyl)-3-pyrazolyl]-1-oxopropane-1-phosphonic acid dimethyl ester in 15 ml of diethyl ether and 10 ml of dichloromethane is added dropwise to a solution of 0.55 g of dimethyl phosphite and 50 mg of diethylamine in 10 ml of diethyl ether. The mixture is then stirred for 3 days at 0° C., worked up as usual, and the residue recrystallized from ethanol, thus obtaining 1 g of 3-[4-(4-chlorophenyl)-1-(4-fluorophenyl)-3-pyrazolyl]-1-hydroxypropane-1,1-bis(phosphonic acid dimethyl ester), mp 131° C.

EXAMPLE 22

At 0° C., 0.34 g of iodotrimethylsilane is added to a suspension of 0.22 g of 3-[4-(4-chlorophenyl)-1-(4-fluorophenyl)-3-pyrazolyl]-1-hydroxypropane-1,1-bis(phosphonic acid dimethyl ester) in 4 ml of tetrachloromethane, and the mixture is stirred for one hour at 0° C. and another 2 hours at room temperature. The reaction mixture is then concentrated and the residue recrystallized from ethanol, yielding 130 mg of 3-[4-(4-chlorophenyl)-1-(4-fluorophenyl)-3-pyrazolyl]-1-hydroxypropane-1,1-diphosphonic acid, mp 223° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A diphosphonic acid derivative of the formula

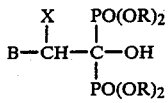

wherein

R is hydrogen, an alkali metal atom, an alkaline earth metal atom, or alkyl of 1–4 carbon atoms, X is hydrogen, methyl, or ethyl, and B is phenyl substituted in the para-position by cyclohexyl, or 1-pyrrolinyl and, optionally, additionally substituted in the meta-position by fluorine or chlorine; phenyl substituted in the meta-position by benzoyl or phenoxy; or phenyl substituted in the ortho-position by 2,4-dichlorophenoxy or 2,6-dichlorophenylamino.

2. A diphosphonic acid derivative of the formula

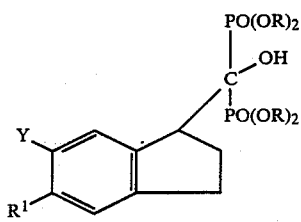

wherein

R is hydrogen, an alkali metal atom, an alkaline earth metal atom, or alkyl of 1–4 carbon atoms, $R^1$ is cyclohexyl or cyclopentylmethyl, and Y is hydrogen or chlorine.

3. A diphosphonic acid derivative of the formula

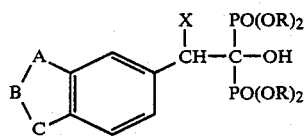

wherein

R is hydrogen, an alkali metal atom, an alkaline earth metal atom, or alkyl of 1–4 carbon atoms, X is hydrogen, methyl or ethyl, and

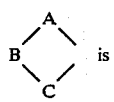 is

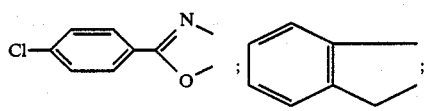

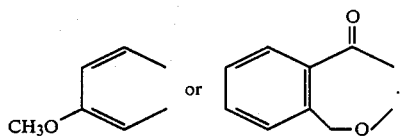

4. A diphosphonic acid derivative of the formula

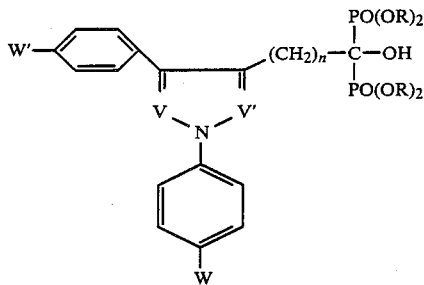

wherein n is 1, 2, or 3,

R is hydrogen, an alkali metal atom, an alkaline earth metal atom, or alkyl of 1–4 carbon atoms, W and W' are identical or different and each is hydrogen, fluorine or chlorine, and one of V and V' is nitrogen and the other is methyne optionally substituted by phenyl.

5. A diphosphonic acid derivative of the formula

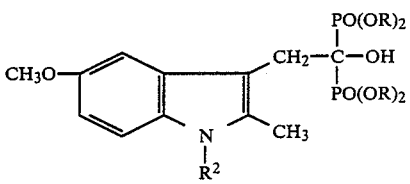

wherein

R is hydrogen, an alkali metal atom, an alkaline earth metal atom, or alkyl of 1–4 carbon atoms, and $R^2$ is p-chlorobenzoyl or cinnamoyl.

6. 2-[1-(4-Chlorobenzoyl)-5-methoxy-2-methyl-3-indolyl]-1-hydroxyethane-1,1-bis(phosphonic acid dimethyl ester), or 2-[1-(4-chlorobenzoyl)-5-methoxy-2-methyl-3-indolyl]-1-hydroxyethane-1,1-diphosphonic acid, compounds of claim 5.

7. 2-(6-Methoxy-2-naphthyl)-1-hydroxypropane-1,1-bis(phosphonic acid dimethyl ester), or 2-(6-methoxy-2-naphthyl)-1-hydroxypropane-1,1-diphosphonic acid, compounds of claim 3.

8. 2-(11-Oxo-2-dibenz[b,f]oxepinyl)-1-hydroxyethane-1,1-bis(phosphonic acid dimethyl ester), or 2-(11-oxo-2-benz[b,f]oxepinyl)-1-hydroxyethane-1,1-diphosphonic acid, compounds of claim 3.

9. (6-Chloro-5-cyclopentylmethyl-1-indanyl)hydroxymethanebis(phosphonic acid diethyl ester), or (6-chloro-5-cyclopentylmethyl-1-indanyl)hydroxymethanediphosphonic acid, compounds of claim 2.

10. 2-[2-(2,6-Dichlorophenylamino)phenyl]-1-hydroxyethane-1,1-bis(phosphonic acid dimethyl ester), or 2-[2-(2,6-dichlorophenylamino)phenyl]-1-hydroxyethane-1,1-diphosphonic acid, compounds of claim 1.

11. 2-[4-(4-Chlorophenyl)-1-(4-fluorophenyl)-3-pyrazolyl]-1-hydroxyethane-1,1-bis(phosphonic acid diethyl ester), 2-[4-(4-Chlorophenyl)-1-(4-fluorophenyl)-3-pyrazolyl]-1-hydroxyethane-1,1-diphosphonic acid, or the disodium salt thereof, compounds of claim 4.

12. 2-[3-(4-Chlorophenyl)-1-phenyl-3-pyrazolyl]-1-hydroxyethane-1,1-bis(phosphonic acid dimethyl ester), or 2-[3-(4-chlorophenyl)-1-phenyl-3-pyrazolyl]-1-hydroxyethane-1,1-diphosphonic acid, compounds of claim 4.

13. 3-[4-(4-Chlorophenyl)-1-(4-fluorophenyl)-3-pyrazolyl]-1-hydroxypropane-1,1-bis(phosphonic acid dimethyl ester, or 3-[4-(4-chlorophenyl)-1-(4-fluorophenyl)-3-pyrazolyl]-1-(hydroxypropane-1,1-diphosphonic acid, compounds of claim 4.

14. A diphosphonic acid derivative of the formula

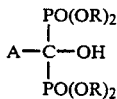

wherein

R is hydrogen, an alkali metal atom, an alkaline earth metal atom, or alkyl of 1-4 carbon atoms and A is the structural moiety of a carboxylic acid, ACOOH, to which the carboxy group is attached, wherein the carboxylic acid has antiinflammatory or antiphlogistic activity and is cliprofen, suprofen, indoprofen, carprofen, metiazic acid, bufezolac, isofezolac, tiaprofenic acid, zomepirac, tolmetin, clopirac, fenclozic acid, fentiazac or sulindac;

or when R is H, a physiologically acceptable salt thereof with an organic base.

15. A pharmaceutical composition comprising an antiinflammatorily effective amount of a compound of the formula

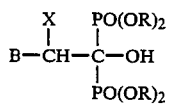

wherein

R is hydrogen, an alkali metal atom, an alkaline earth metal atom, or alkyl of 1-4 carbon atoms, X is hydrogen, methyl, or ethyl, and B is phenyl substituted in the para-position by cyclohexyl, or 1-pyrrolinyl and, optionally, additionally substituted in the meta-position by fluorine or chlorine; phenyl substituted in the meta-position by benzoyl or phenoxy; or phenyl substituted in the ortho-position by 2,4-dichlorophenoxy or 2,6-dichlorophenylamino; or

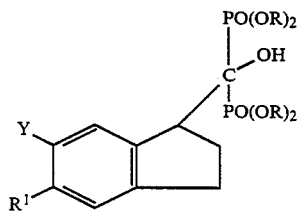

wherein

R is hydrogen, an alkali metal atom, an alkaline earth metal atom, or alkyl of 1-4 carbon atoms, $R^1$ is cyclohexyl or cyclopentylmethyl, and Y is hydrogen or chlorine; or

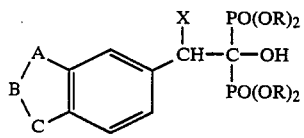

wherein

R is hydrogen, an alkali metal atom, an alkaline earth metal atom, or alkyl of 1-4 carbon atoms, X is hydrogen, methyl or ethyl, and

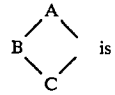 is

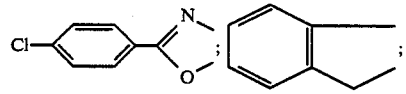

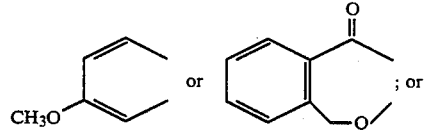

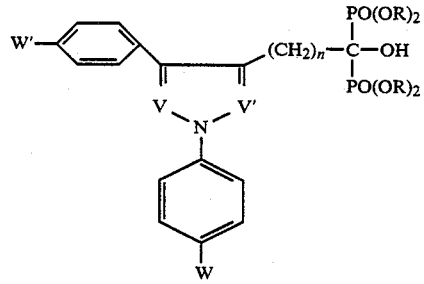

wherein n is 1, 2, or 3,

R is hydrogen, an alkali metal atom, an alkaline earth metal atom, or alkyl of 1-4 carbon atoms, W and W' are identical or different and each is hydrogen, fluorine or chlorine, and one of V or V' is nitrogen and the other is methyne optionally substituted by phenyl; or

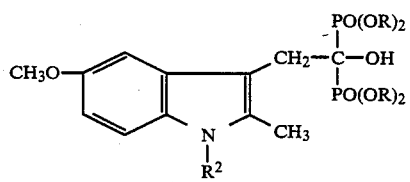

wherein

R is hydrogen, an alkali metal atom, an alkaline earth metal atom, or alkyl of 1-4 carbon atoms, and $R^2$ is p-chlorobenzoyl or cinnamoyl;

and a pharmacologically acceptable adjuvant.

16. A method of treating inflammation in a patient in need of such treatment comprising administering to the patient an antiinflammatorily effective amount of a diphosphonic acid derivative of the formula

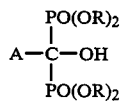

wherein

R is hydrogen, an alkali metal atom, an alkaline earth metal atom, or alkyl of 1-4 carbon atoms and A is the structural moiety of a carboxylic acid, ACOOH, to which the carboxy group is attached, wherein the carboxylic acid has antiinflammatory or antiphlogistic activity and A contains an aromatic or heteroaromatic group;

or when R is H, a physiologically acceptable salt thereof with an organic base.

17. A method of claim 16 wherein the patient is suffering from arthritis.

18. A method of claim 16, wherein the diphosphonic acid derivative is of the formula

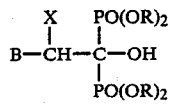

wherein

R is hydrogen, an alkali metal atom, an alkaline earth metal atom, or alkyl of 1–4 carbon atoms, X is hydrogen, methyl or ethyl, and B is phenyl substituted in the para-position by isobutyl, cyclohexyl, $C_{1-4}$-alkoxy, or 1-pyrrolinyl and, optionally, additionally substituted in the meta-position by fluorine or chlorine; phenyl substituted in the meta-position by benzoyl or phenoxy; or phenyl substituted or in the ortho-position by 2,4-dichlorophenoxy or 2,6-dichlorophenylamino; or

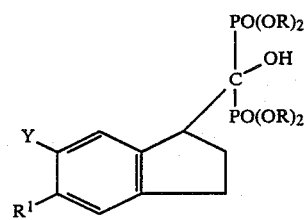

wherein

R is hydrogen, an alkali metal atom, an alkaline earth metal atom, or alkyl of 1–4 carbon atoms, $R^1$ is cyclohexyl or cyclopentylmethyl, and Y is hydrogen or chlorine; or

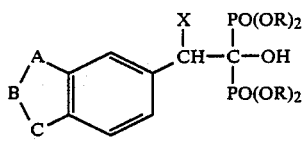

wherein

R is hydrogen, an alkali metal atom, an alkaline earth metal atom, or alkyl of 1–4 carbon atoms, X is hydrogen, methyl or ethyl, and

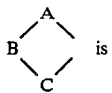

is

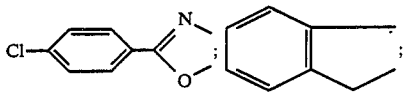

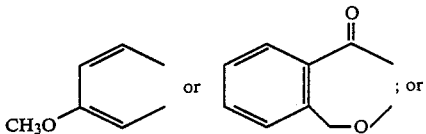

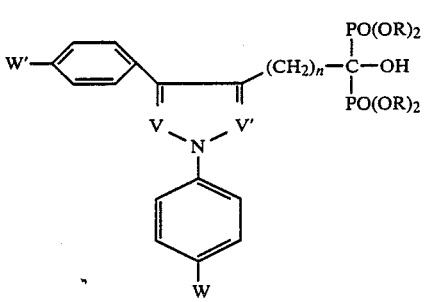

wherein n is 1, 2, or 3,

R is hydrogen, an alkali metal atom, an alkaline earth metal atom, or alkyl of 1–4 carbon atoms, W and W' are identical or different and each is hydrogen, fluorine or chlorine, and one of V or V' is nitrogen and the other is methyne optionally substituted by phenyl; or

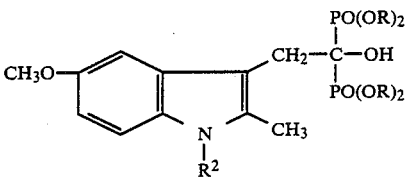

wherein

R is hydrogen, an alkali metal atom, an alkaline earth metal atom, or alkyl of 1–4 carbon atoms, and $R^2$ is p-chlorobenzoyl or cinnamoyl.

* * * * *